US00PP31979P2

(12) United States Plant Patent
Van Swieten

(10) Patent No.: US PP31,979 P2
(45) Date of Patent: Jul. 14, 2020

(54) ***PHALAENOPSIS* ORCHID PLANT NAMED 'PHALFROFE'**

(50) Latin Name: ***Phalaenopsis* hybrid**
Varietal Denomination: PHALFROFE

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,737

(22) Filed: May 30, 2019

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'PHALFROFE', QZ PBR 50608, filing date Sep. 28, 2017.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALFROFE', particularly characterized by having light purple, shaded flowers with red-purple lips, 1 to 3 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALFROFE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFROFE'.

The new *Phalaenopsis* plant is a product of a planned breeding program conducted by the inventor in Bleiswijk, the Netherlands. The objective of this breeding program was to create a new *Phalaenopsis* plant with numerous attractive light purple, shaded flowers with red-purple lips, suitable for potted plant production.

The new *Phalaenopsis* plant 'PHALFROFE' is a result of cross-pollination made by the inventor in March 2008 in Bleiswijk, the Netherlands, of the proprietary female, or seed parent, *Phalaenopsis* hybrid '11968-04' (unpatented) with the proprietary male, or pollen parent, *Phalaenopsis* hybrid '01-2077' (unpatented).

The new *Phalaenopsis* was selected by the inventor as a single plant within the progeny of the stated cross-pollination in a controlled greenhouse in Bleiswijk, the Netherlands, in August 2010. Asexual reproduction of the new *Phalaenopsis* plant by meristem tissue culture since 2013 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Sep. 28, 2017, by Applicant who obtained the subject matter disclosed directly from the Inventor. 'PHALFROFE' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALFROFE' as a new and distinct variety of *Phalaenopsis* plant:

1) Light purple, shaded flowers with red-purple lips;
2) 1 to 3 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in March 2019. Colors in the photographs may differ from the color values cited in the detailed botanical description, which accurately describe the actual colors of the new variety.

DESCRIPTION OF THE NEW VARIETY

Figure 1:
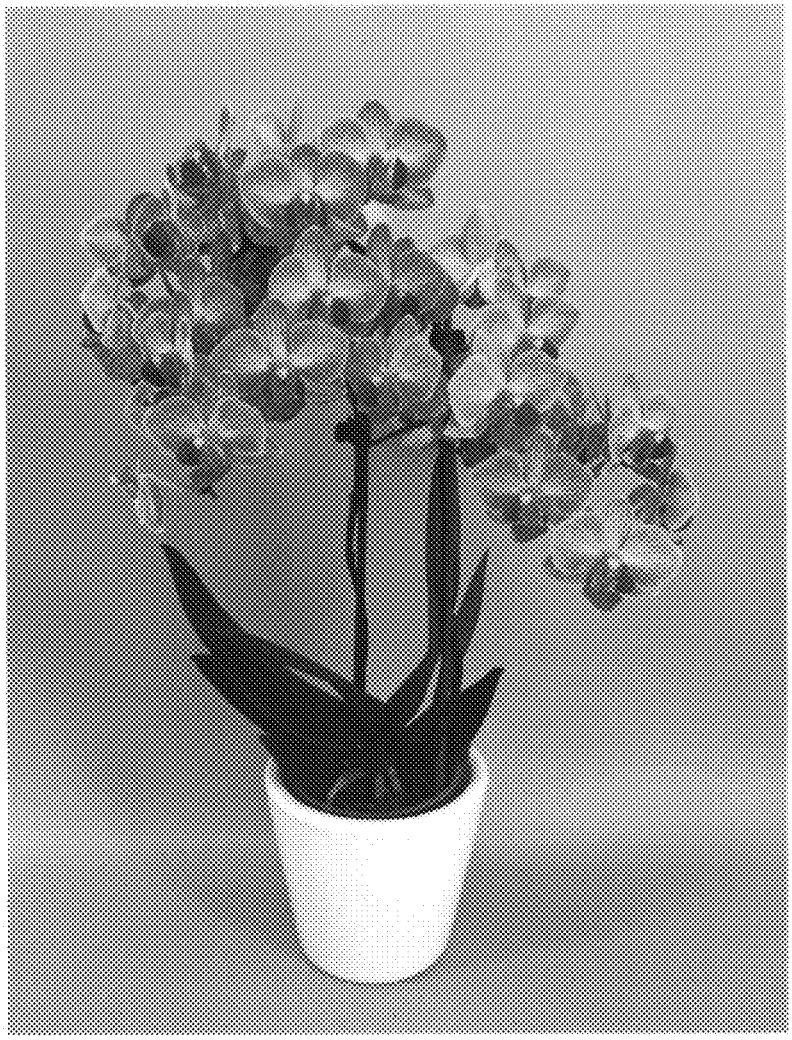
FIG. 1 shows the overall plant habit, including blooms and foliage of 'PHALFROFE'.
Figure 2:
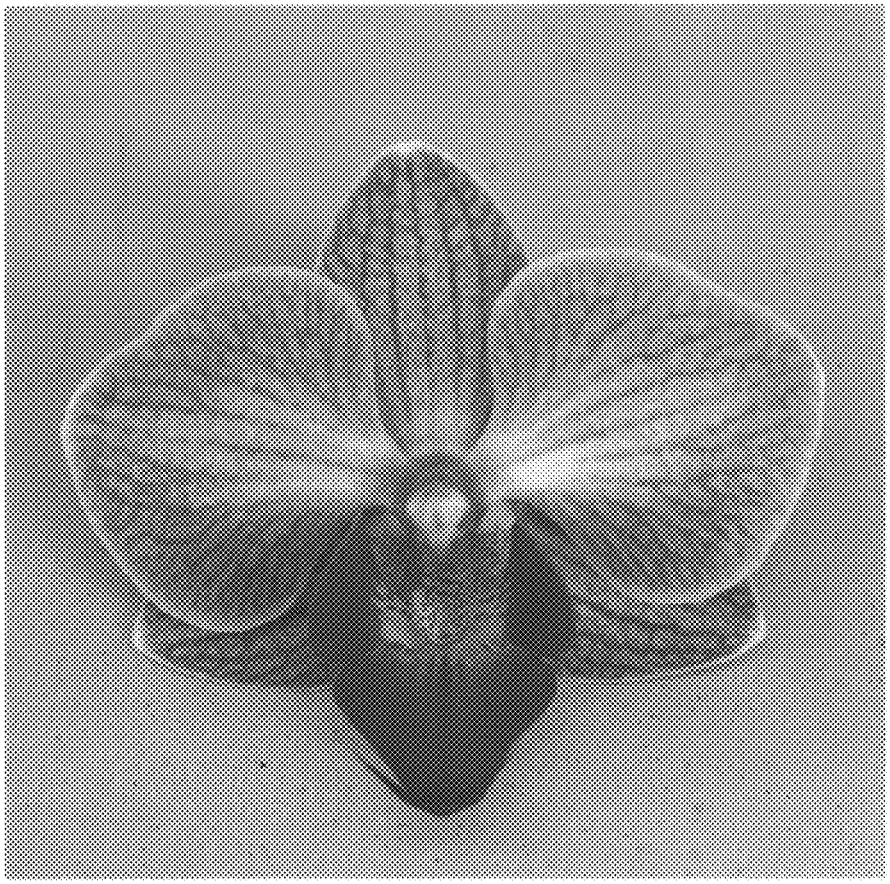
FIG. 2 shows a close-up of a flower of 'PHALFROFE'.
Figure 3:
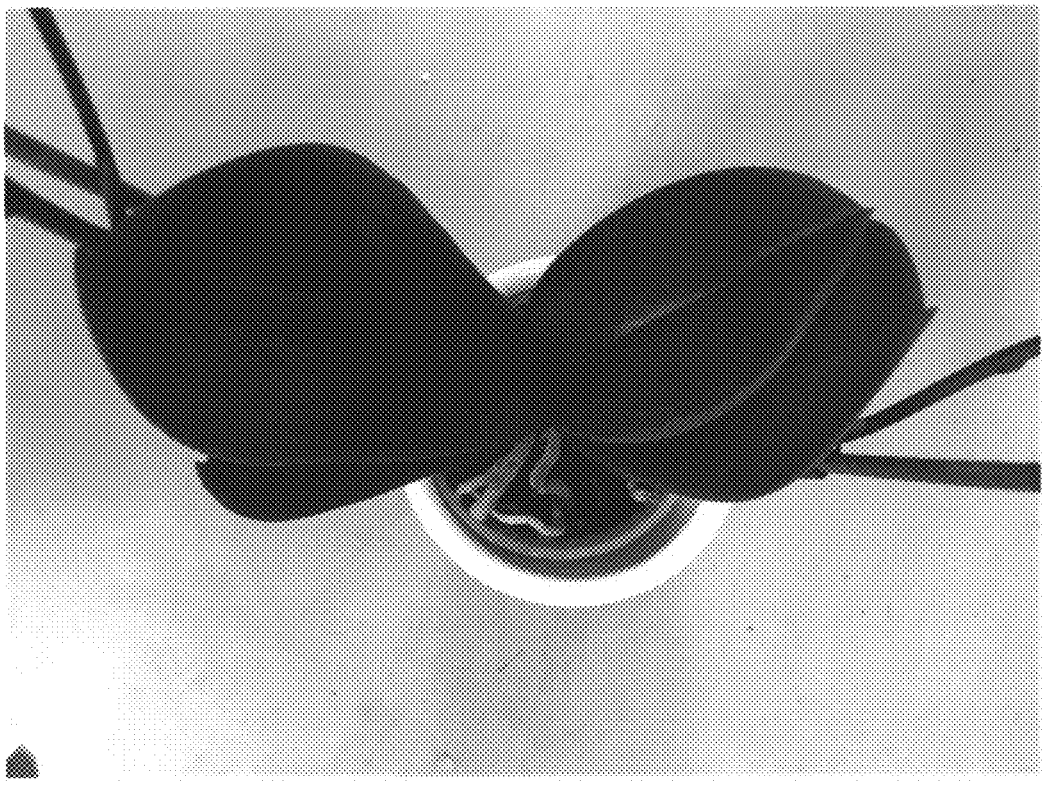
FIG. 3 shows an overhead view of the leaves of 'PHALFROFE'.

The following detailed description sets forth the distinctive characteristics of 'PHALFROFE'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2019 on flowering plants which were planted in 9-centimeter (diameter) pots. After in-vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALFROFE'.

Parentage:
- *Female parent*.—*Phalaenopsis* cultivar '11968-04' (unpatented).
- *Male parent*.—*Phalaenopsis* cultivar '01-2077' (unpatented).

Propagation:
- *Type*.—Meristem tissue culture.

Roots:
- *Root description*.—Greyed-green (between RHS 190B and 190C) colored roots with branching lateral roots having yellow-green (RHS N144C) colored root tips.

Plant:
- *Commercial crop time to flowering*.—Following asexual propagation (in-vitro), the rooted cuttings grow for 18-20 weeks. After transplantation into 9-cm pots, the plants are finished after 40 to 42 weeks.
- *Growth habit of peduncle*.—Upright to slightly pendant with panicle inflorescence.
- *Height* (*from soil level to top of inflorescence*).—Approximately 34.0 cm to 39.0 cm.
- *Width* (*measured from leaf tips*).—About 18.0 cm to 20.0 cm.
- *Vigor*.—Moderate.

Leaves:
- *Mature leaves*.—Quantity per plant: 7 to 9 leaves are produced before flowering. Length (fully expanded): 14.0 cm to 16.0 cm. Width: 6.0 cm to 7.0 cm. Shape: Oblong. Base shape: Moderately elongated. Apex: Obtuse unequal. Leaf blade angle with the petiole (measured from the horizontal position): Between 25 degrees and 40 degrees. Leaf margin: Entire. Color: Upper surface: RHS 147A. Lower surface: RHS 146A. Texture (both upper and lower surfaces): Rough. Thickness: 1.9 mm to 2.3 mm. Variegation: Absent. Venation: Pattern: Parallel. Color of the midvein: Upper surface: RHS 147A. Lower surface: RHS 146B.

Peduncle:
- *Quantity per plant*.—1 to 3.
- *Number of flowers per peduncle*.—18 to 32.
- *Length*.—34.0 cm to 39.0 cm.
- *Diameter*.—3.5 mm to 4.3 mm.
- *Strength*.—Strong.
- *Aspect*.—Upright to slightly pendant.
- *Texture*.—Smooth.
- *Color*.—Mix of green (RHS 146B) and brown (RHS N200A).
- *Internode length*.—2.0 cm to 3.0 cm.

Inflorescence description:
- *Appearance*.—Upright to slightly pendant, panicle inflorescence with bilaterally symmetrical flowers that open in succession beginning with the lowermost flower.
- *Number of inflorescences*.—1 to 3.
- *Inflorescence size*.—Height (from base to tip): 170.0 mm to 220.0 mm.
- *Flowering time*.—First flowers can be expected 7 to 8 months after planting in a 9-cm pot.
- *Flower*.—Height: 40.0 mm to 45.0 mm. Diameter: 50.0 mm to 55.0 mm. Depth of lip: 15.0 mm to 17.0 mm.
- *Flower longevity*.—On the plant: 9 to 15 weeks.
- *Fragrance*.—Absent.
- *Flower bud*.—Average size: Medium. Length: 14.0 mm to 16.0 mm. Width: 12.0 mm to 14.0 mm. Shape: Egg shaped. Color: Light yellow-green (RHS 145C) with a touch of purplish-red (RHS N77B).
- *Petals*.—Arrangement: Open/free. Shape: Semi-circular. Apex: Obtuse asymmetric. Margin: Entire. Length (from base to tip): 23.0 mm to 25.0 mm. Width: 25.0 mm to 27.0 mm. Position of the broadest part of the petal: Toward the base. Color (when fully opened): Upper surface: Basic color: Very light purple (RHS 76B). Over color: Light reddish-purple shade (RHS N78B) and reddish-purple stripes (RHS N78B). Lower surface: Basic color: Very light purple (RHS 76B). Over color: Purplish-pink shade (RHS N78C) and reddish-purple stripes (RHS N78B).
- *Dorsal sepal*.—Shape: Elliptic. Apex: Obtuse to slightly emarginated symmetric. Margin: Entire. Length (from base to tip): 24.0 mm to 26.0 mm. Width: 26.0 mm to 28.0 mm. Color (when fully opened): Upper surface: Basic color: Light purple (RHS N75D). Over color: Reddish-purple stripes (RHS N78B). Lower surface: Basic color: Light purple (RHS N75D). Over color: Reddish-purple stripes (RHS N78B to N78C).
- *Lateral sepals*.—Shape: Ovate. Apex: Obtuse asymmetric. Margin: Entire. Length (from base to tip): 23.0 mm to 25.0 mm. Width: 15.0 mm to 17.0 mm. Color (when fully opened): Upper surface: Basic color: Light purple (RHS N75C). Over color: Slightly light yellow-green (RHS 157A) at the base with red dots (RHS 182B); reddish-purple stripes (RHS N78A). Lower surface: Basic color: Light purple (RHS N75D). Over color: Purplish-pink stripes (RHS N78C).

*Labellum* (*lip*).—Whiskers: Present. Length of whiskers: 2.0 mm to 4.0 mm. Color of whiskers: Reddish-purple (RHS N78A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 14.0 mm to 16.0 mm. Width: 8.0 mm to 10.0 mm. Color: Slightly white (RHS NN155C) at the base; striped (RHS 175A); reddish-purple (RHS N78A) on one side; dark red (RHS 59A) toward other side.

*Apical lobe*.—Shape: Ovate. Margin: Entire. Length: 15.0 mm to 17.0 mm. Width: 14.0 mm to 16.0 mm. Color: Slightly orange-yellow (RHS 163A) at the base; red (RHS 185A) and reddish-purple (RHS NN78A) toward whiskers.

*Callus*.—Average size: Small. Height: 4.0 mm to 5.0 mm. Length: 4.0 mm to 5.0 mm. Width: 3.0 mm to 4.0 mm. Color: Greenish-yellow (RHS 8C); dotted (RHS 176A).

Reproductive organs:

*Column*.—Length: 7.0 mm to 9.0 mm. Diameter: 3.8 mm to 4.1 mm. Color: Reddish-purple (RHS N78B).

*Pollinia*.—Quantity: 2. Diameter: 0.8 mm to 1.0 mm. Color: Orange (RHS 24A).

*Ovary*.—Length: 8.0 mm to 10.0 mm. Diameter: 1.8 mm to 2.1 mm. Color: Light yellow-green (RHS 145C) and very light purple (RHS 76C) toward the flower.

*Pedicel*.—Length: 33.0 mm to 35.0 mm. Diameter: 2.2 mm to 2.4 mm. Color: Brown (RHS N199B) at the base and light yellow-green (RHS 145B to 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFROFE' differs from female parent plant '11968-04' (unpatented) in that 'PHALFROFE' has reddish-purple columns, reddish-purple whiskers, and flowers with a basic color of very light purple that have a striped and shaded pattern, whereas '11968-04' has white columns, white whiskers, and flowers with a basic color of white that have an even pattern.

'PHALFROFE' differs from male parent plant '01-2077' (unpatented) in that 'PHALFROFE' has greenish-yellow and dotted (RHS 176A) calluses, reddish-purple columns, and flowers with a basic color of very light purple that have a striped and shaded pattern, whereas '01-2077' has dark red calluses, columns that are white at the base and tip and purplish-pink in the middle, and flowers with a basic color of white that have a flecked pattern.

'PHALFROFE' is most similar to the commercial *Phalaenopsis* plants named 'PHALDONFI' (U.S. Plant Pat. No. 26,066) and 'PHALCRYO' (U.S. Plant Pat. No. 28,068). 'PHALFROFE' differs from the commercial variety 'PHALDONFI' in that 'PHALFROFE' has reddish-purple columns, weakly spatulate lateral lobes, and ovate apical lobes, whereas 'PHALDONFI' has purple columns, spatulate lateral lobes, and obdeltoid apical lobes.

'PHALFROFE' differs from the commercial variety 'PHALCRYO' in that 'PHALFROFE' has flowers with a main color of very light purple, reddish-purple (RHS N78A) whiskers, and weakly spatulate lateral lobes, whereas 'PHALCRYO' has flowers with a main color of white, red-purple (RHS 64A) whiskers with small yellow tips, and spatulate lateral lobes.

I claim:

1. A new and distinct variety of *Phalaenopsis* plant named 'PHALFROFE', substantially as described and illustrated herein.

* * * * *